(12) United States Patent
Stanzel et al.

(10) Patent No.: US 6,440,296 B1
(45) Date of Patent: Aug. 27, 2002

(54) MICROSTRUCTURED BIOSENSOR, USE OF THE BIOSENSOR AND PROCESS FOR THE IMMOBILIZATION OF BIOCATALYSTS

(75) Inventors: Manfred Stanzel, Erlangen; Walter Gumbrecht, Herzogenaurach, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/536,027

(22) Filed: Mar. 27, 2000

Related U.S. Application Data

(63) Continuation of application No. PCT/DE98/02719, filed on Sep. 14, 1998.

(30) Foreign Application Priority Data

Sep. 26, 1997 (DE) .......................... 197 42 690

(51) Int. Cl.$^7$ .................. G01N 27/26; C12N 11/02
(52) U.S. Cl. ................. 205/777.5; 204/403; 435/177; 435/180
(58) Field of Search ............ 204/403; 205/777.5; 435/177, 179, 180, 182, 176

(56) References Cited

U.S. PATENT DOCUMENTS 4,659,667 A * 4/1987 Brewer et al. ............. 435/222

FOREIGN PATENT DOCUMENTS

| EP | 0 216 467 A2 | 4/1987 |
| EP | 0 415 124 A2 | 3/1991 |
| EP | 0 588 153 B1 | 3/1994 |
| EP | 0 636 879 A2 | 2/1995 |
| EP | 0 872 729 A1 | 10/1998 |
| GB | 2 230 865 A | 10/1990 |

OTHER PUBLICATIONS

"Biosensors: Recent Trends, A Review", XP–002096648, Analyst, Nov. 1992, vol. 117, pp. 1657–1670, as mentioned on p. 2 of the specification.

"Academic Spectrum, Biosensoren" (Schneller et al.), dated Sep. 1992, XP–002096649, pp. 99–103, pertains to trends and perspectives on the application of enzyme– and cell sensors, as mentioned on p. 1 of the specification.

* cited by examiner

*Primary Examiner*—T. Tung
*Assistant Examiner*—Alex Noguerola
(74) *Attorney, Agent, or Firm*—Laurence A. Greenberg; Werner H. Stemer; Ralph E. Locher

(57) ABSTRACT

A biosensor is used for measuring principal metabolites in blood and other substances. The biosensor has a special structure formed of a two-layer enzymatic membrane with a considerably increased functionality compared with enzymatic membranes of the prior art.

7 Claims, 1 Drawing Sheet

MICROSTRUCTURED BIOSENSOR, USE OF THE BIOSENSOR AND PROCESS FOR THE IMMOBILIZATION OF BIOCATALYSTS

CROSS-REFERENCE TO RELATED APPLICATION

This is a continuation of copending International Application PCT/DE98/02719, filed Sep. 14, 1998, which designated the United States.

BACKGROUND OF THE INVENTION

1. Field of the Invention

The invention concerns a microstructured, planar biosensor, in particular a biosensor with an enzyme as a biocatalyst. The invention also concerns the use of the biosensor and a process for immobilizing biocatalysts.

Analytical devices are already known with detection layers of enzymatic membranes or enzyme layers (both terms being used synonymously here), through which the change in hydrogen peroxide or oxygen concentration resulting from an enzymatic turnover, e.g. of oxygen, can be determined electrochemically or amperometrically (F. Scheller et al., "Enzym- und Zellsensoren—Anwendungen, Trends und Perspektiven", Spektrum der Wissenschaft, September 1992, pages 99 to 103). The functionality, for example the saturation characteristics and sensitivity, of such a biosensor depends primarily on the quality of the enzymatic membrane used. A number of criteria must be met in fabricating the membrane (P. Vadgama and P. W. Crump, titled "Biosensors: Recent Trends", Analyst, November 1992, Vol. 117, pages 1657 to 1670). The maximum possible amount of active enzyme must be immobilized or bound in such a way that it largely remains functional and active while, at the same time, being attached to the membrane. A number of techniques have been developed for achieving this binding of the enzyme in the membrane in as gentle a way as possible. The following methods are used: adsorption, ionic binding, absorption, enclosure in microcapsules or in membranes, and covalent binding to carrier substances.

On the one hand, fabrication of the enzymatic membrane takes place through the enzyme being physically bound in polymeric "gels", e.g. poly(hydroxyethyl methacrylate), in which the enzyme is retained as if in nets. This method suffers the disadvantage that interactions always arise between the gel molecules and the enzymatic proteins, which affect the flexibility of the three-dimensional structure and thereby negatively influence the activity of the enzymes. Alternatively, techniques are used through which the enzymatic proteins are attached directly to polymeric carriers over covalent chemical bonds. In this case, of course, the dynamics of the tertiary structure of the protein is influenced to an even greater extent by cross-linking between the amino-acid side-chains of the enzyme and the active groups of the carrier. Since, however, this structure is an important requirement for the activity of the enzyme, such a restriction of the structural flexibility is associated with partial inactivation of the enzyme.

European Patent EP 0 588 153 B1 discloses a structure of a planar, microstructured gas sensor chip with a first, inner, and a second, outer, limiting structure. This structure enables the formation of a pot & lid structure for a measuring solution (electrolyte solution) in that the electrolyte solution is placed in the first, inner limiting structure (pot) and a hydrophobic and protective material (lid) is placed in the second, outer limiting structure in such a way that it completely covers the electrolyte solution together with the first, inner limiting structure. This planar sensor chip is used for the determination of electrochemical gases such as oxygen and carbon dioxide.

Up to now there has been no pot & lid structure for biosensor determinations with a sensor chip of this kind because only the enzymatic membrane, which is formed as a single homogeneous layer, was available as a detection layer ("measuring solution"). Thus up now, the two limiting structures could not be exploited for determinations using biosensors because formation of the pot & lid structure requires the existence of two layers instead of a single homogeneous layer.

SUMMARY OF THE INVENTION

It is accordingly an object of the invention to provide a microstructured biosensor, use of the biosensor and a process for the immobilization of biocatalysts that overcome the above-mentioned disadvantages of the prior art devices and methods of this general type, which has improved functionality, whose detection layer consists of two layers and in which the dynamics of the tertiary structure of the enzymes remains unchanged. Finally, the object of the invention is to provide a process with which a pot & lid structure can be fabricated on a sensor chip with an inner and an outer limiting structure.

With the foregoing and other objects in view there is provided, in accordance with the invention, a microstructured, planar biosensor, in which a biomolecular turnover to be measured can be determined electrochemically, the biosensor including:

a planar substrate;

a first, inner limiting structure defining a first interior space disposed on the planar substrate;

an enzymatic layer having an enzyme in a crystalline form disposed in the first interior space;

a second, outer limiting structure defining a second interior space disposed on the planar substrate; and a polymeric hydrophilic covering layer disposed in the second interior space completely covering the first, inner limiting structure containing the enzymatic layer.

The subject of the invention is therefore a microstructured, planar biosensor with which the biomolecular turnover to be measured is determined electrochemically, whereby the sensor contains at least two limiting structures on a planar substrate. A first, inner limiting structure filled with an enzymatic membrane, and a second, outer limiting structure filled with a polymeric covering layer completely covering the first limiting structure with the enzymatic membrane is provided.

A further subject of the invention is the use of the biosensor in medicine, namely for the minimally invasive determination of principal metabolites in blood, such as glucose and lactate.

The final subject of the invention is a process for the immobilization of biocatalysts in which, in a first step, the biocatalyst in a liquid solution is filled onto a substrate in a first, inner limiting structure, is dried there in a second step, and is finally coated with a polymerizable covering layer in a third step.

Other features which are considered as characteristic for the invention are set forth in the appended claims.

Although the invention is illustrated and described herein as embodied in a microstructured biosensor, use of the biosensor and a process for the immobilization of biocatalysts, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

PREFERRED EMBODIMENT OF THE INVENTION

Figure 1:
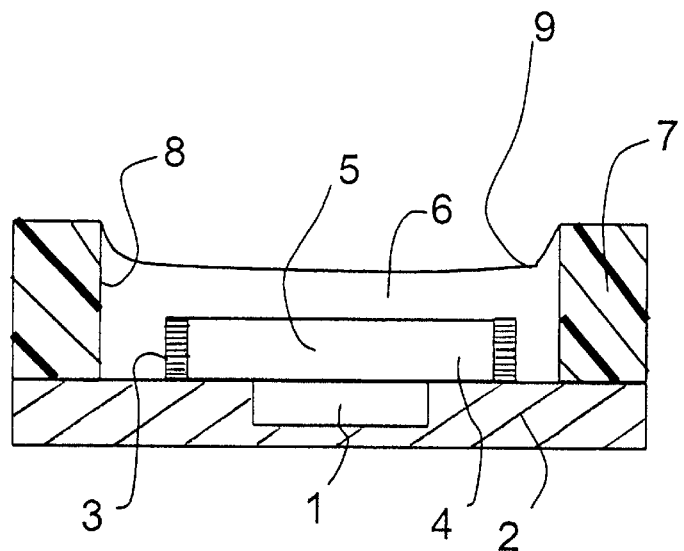
FIG. 1 is a diagrammatic, sectional view of a biosensor according to the invention.
Figure 2:
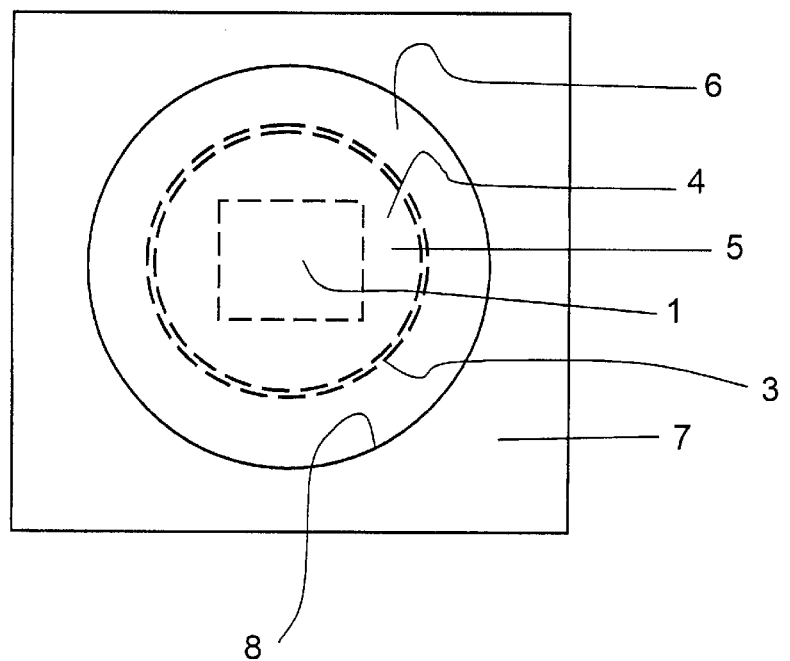
FIG. 2 is a top plan view of the biosensor.

In all the figures of the drawing, sub-features and integral parts that correspond to one another bear the same reference symbol in each case. Referring now to the figures of the drawings in detail and first, particularly, to FIG. 1 thereof, there is shown a biosensor formed of a sensor 1 disposed on a planar substrate 2. A first, inner limiting structure 3 is disposed on the substrate 2 and defines a first interior 4. An enzyme 5, preferably used as a biocatalyst 5, especially preferred being the use of an enzyme that requires oxygen as co-substrate (coenzyme), such as glucose oxidase or lactate oxidase, is disposed in the first interior 4.

The enzymatic membrane 5 preferably contains a buffer solution that includes triethylene glycol and a phosphate buffer. An example for this is a solution of 5000 U of glucose oxidase, 120 µl of a buffer solution (concentration 100 mmol/l, pH 7) and 30 µl of triethylene glycol.

It is also advantageous if a planarizing additive, such as polyvinylpyrrolidone (PVP) is added to the enzymatic membrane 5.

Before application of a covering layer 6 the solution with the enzymatic membrane or enzymatic layer 5 must be sufficiently dried till it is crystalline or in the form of a gel. The already cross-linked covering layer 6 is permeable to water so that under operating conditions the biosensor can become moist once again and therefore the enzymes can become active.

A UV-cross-linked coating is preferably used as the covering layer 6. An example thereof is a photo-structurizable hydroxymethyl methacrylate resin (HEMA resin) consisting of a solution of 2.374 g of HEMA, 0.025 g of dimethoxyphenylacetophenone (DMAP) and 0.075 g of tetraethylene glycol methacrylate (TEGM) in 60 µl of triethylene glycol. Other polymerizable materials can also be used, as long as they harden or completely polymerize under conditions that the biocatalyst 5 survives undamaged. The final, i.e. completely polymerized coating must be formed such that it is permeable to all the substances taking part in the reaction, with the exception of the biocatalyst 5. For example, for the determination of glucose it must be permeable to water, oxygen and glucose, but not to the enzyme glucose oxidase.

The biocatalyst 5 in the membrane is preferably as dry as possible, i.e. either crystalline or in the form of a gel. Crystalline in this case refers to the enzymatic membrane 5 that is dry and planar.

The covering layer 6 is delimited by a wall 8 of a second, outer limiting structure 7 defining a second interior 9.

The limiting structures 3, 7 are polymeric structures which, for example, can be formed from a synthetic material such as polyimide. The limiting structures 3, 7 can have different heights or be of the same height.

The invention makes possible a significant improvement in the functionality of biosensors because the biomolecule can move freely in a "pot" (i.e. the first inner limiting structure 3 with the enzyme layer 5) without interfering interactions and is held in the measuring solution by a "lid" (i.e. the covering layer 6). This is particularly apparent in the improved saturation characteristics (measurements are possible up to a glucose concentration of approx. 35 mmol/l) and in the increased sensitivity of the sensor (current densities of >100 nA*l/mmol*mm$^2$ at glucose concentrations of <20 mmol/l) of the biosensor according to the invention.

The sensitivity achieved and the saturation characteristics allow the invention to be used both in medical physiological ranges between 3 and 20 mmol/l (concentration of the substance to be measured) and also in biotechnology, in which—according to application—requirements extend to a range of 100 mmol/l and even higher in extreme cases.

We claim:

1. A microstructured, planar biosensor, in which a biomolecular turnover to be measured can be determined electrochemically, the biosensor comprising:

a planar substrate;

a first, inner limiting structure defining a first interior space disposed on said planar substrate;

an enzymatic layer having an enzyme in a crystalline form disposed in said first interior space;

a second, outer limiting structure defining a second interior space disposed on said planar substrate; and a polymeric hydrophilic covering layer disposed in said second interior space completely covering said first, inner limiting structure containing said enzymatic layer.

2. The biosensor according to claim 1, wherein said enzyme requires oxygen as a co-substrate.

3. The biosensor according to claim 1, wherein said enzymatic layer is disposed in said first interior space by drying a buffer solution containing triethylene glycol and a phosphate buffer added to said enzyme.

4. The biosensor according to claim 1, wherein said polymeric hydrophilic covering layer is a UV cross-linked polymer.

5. The biosensor according to claim 4, wherein said polymeric hydrophilic covering layer is a cross-linked hydroxyethyl methacrylate resin.

6. A method for testing for principal metabolites in blood, which comprises:

providing a biosensor formed of a planar substrate, a first, inner limiting structure defining a first interior space disposed on the planar substrate, an enzymatic layer having an enzyme in a crystalline form disposed in the first interior space, a second, outer limiting structure defining a second interior space disposed on the planar substrate; and a polymeric hydrophilic covering layer disposed in the second interior space completely covering the first, inner limiting structure containing the enzymatic layer; and using the biosensor for minimally invasive determination of a substrate selected from the group consisting of glucose and lactate in blood.

7. A process for immobilization of enzymes, which comprises:

filling an enzyme, in a form of a liquid solution, into a first, inner limiting structure on a substrate;

drying the enzyme initially in the form of the liquid solution into a crystalline form; and coating the enzyme in the crystalline form with a polymerizable hydrophilic covering layer.

\* \* \* \* \*